(12) United States Patent
Efsen et al.

(10) Patent No.: US 11,097,309 B2
(45) Date of Patent: Aug. 24, 2021

(54) SYSTEM AND A METHOD FOR IRRADIATING AN OBJECT

(71) Applicant: EFSEN Engineering A/S, Vedbæk (DK)

(72) Inventors: Thomas Efsen, Charlottenlund (DK); Agge Winther, Copenhagen (DK)

(73) Assignee: EFSEN Engineering A/S, Vedbæk (DK)

( * ) Notice: Subject to any disclaimer, the term of this patent is extended or adjusted under 35 U.S.C. 154(b) by 127 days.

(21) Appl. No.: 16/605,150

(22) PCT Filed: Apr. 23, 2018

(86) PCT No.: PCT/EP2018/060305
§ 371 (c)(1),
(2) Date: Oct. 14, 2019

(87) PCT Pub. No.: WO2018/197397
PCT Pub. Date: Nov. 1, 2018

(65) Prior Publication Data
US 2021/0138504 A1 May 13, 2021

(30) Foreign Application Priority Data
Apr. 28, 2017 (EP) .................... 17168782

(51) Int. Cl.
*G01J 1/42* (2006.01)
*B05D 3/06* (2006.01)
*G01J 1/44* (2006.01)

(52) U.S. Cl.
CPC ............. *B05D 3/067* (2013.01); *G01J 1/429* (2013.01); *G01J 2001/444* (2013.01)

(58) Field of Classification Search
CPC ...... B05D 3/067; G01J 1/429; G01J 2001/444
See application file for complete search history.

(56) References Cited

U.S. PATENT DOCUMENTS

| 4,165,463 A * | 8/1979 | Bowen | G01J 1/429 250/372 |
| 4,208,587 A | 6/1980 | Eastlund et al. | |

(Continued)

FOREIGN PATENT DOCUMENTS

| EP | 0656656 | 6/1995 |
| JP | 2005319172 | 11/2005 |
| WO | WO2018197397 | 11/2018 |

OTHER PUBLICATIONS

Anonymous, "Charaterization of photocurable coatings using fluorescence probes", Retrieved from the Internet on Dec. 11, 2019, https://www.thefreelibrary.com/characterization+of+photocurable+coatings+using+fluorescence+probes.-a018158432, pp. 1-9, (2019).

*Primary Examiner* — Kiho Kim
(74) *Attorney, Agent, or Firm* — McHale & Slavin, P.A.

(57) ABSTRACT

A system and a method for irradiating an object and potentially for controlling the irradiation or other conditions relating to an effect of the irradiation. A sensor is translated along a longitudinal direction of the radiation emitter and in a space between the radiation emitter and the objects irradiated to arrive at information relating to a parameter relating to the effect of the irradiation, such as the radiation, and derived in the space between the radiation emitter and the objects irradiated. Calibrating the sensor readings and adjusting the radiating emitter output, thereby controlling the irradiation.

15 Claims, 1 Drawing Sheet

(56) References Cited

U.S. PATENT DOCUMENTS

| | | | |
|---|---|---|---|
| 4,665,627 A | 5/1987 | Wilde et al. | |
| 6,555,823 B2 | 4/2003 | Kuhns et al. | |
| 6,566,656 B2 | 5/2003 | May et al. | |
| 9,448,108 B2 | 9/2016 | Jing | |
| 2003/0039579 A1 | 2/2003 | Lambert et al. | |
| 2004/0035529 A1 | 2/2004 | Grimbergen | |
| 2005/0031485 A1 | 2/2005 | Wen | |
| 2006/0076502 A1* | 4/2006 | Boord | H01L 31/1035 250/372 |
| 2013/0026381 A1 | 1/2013 | Huang et al. | |
| 2014/0328579 A1 | 11/2014 | Childers | |
| 2017/0105257 A1 | 4/2017 | Yue et al. | |

* cited by examiner

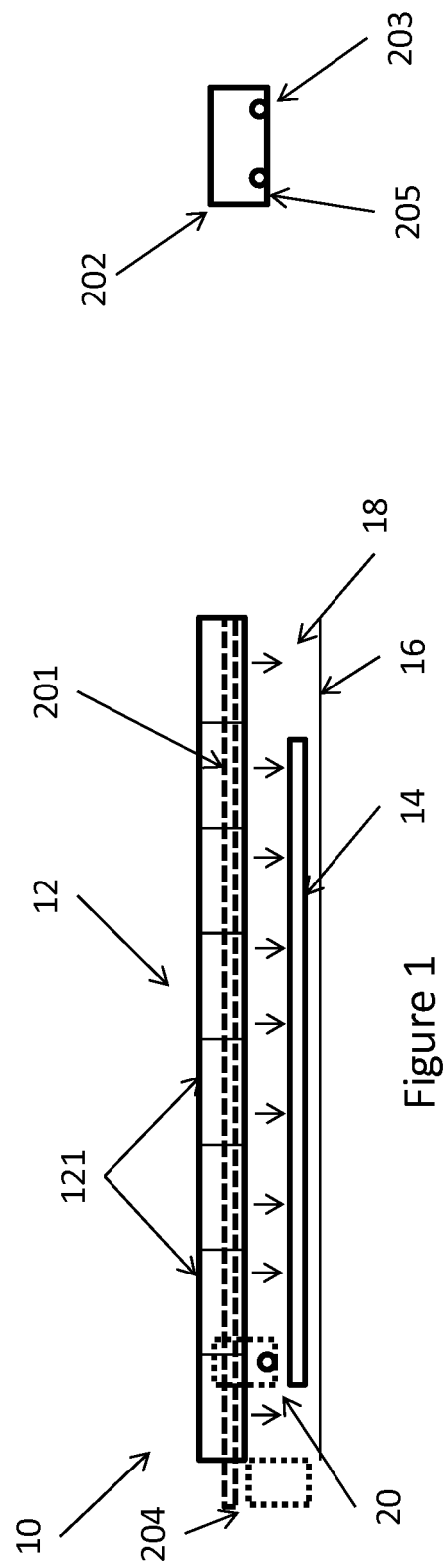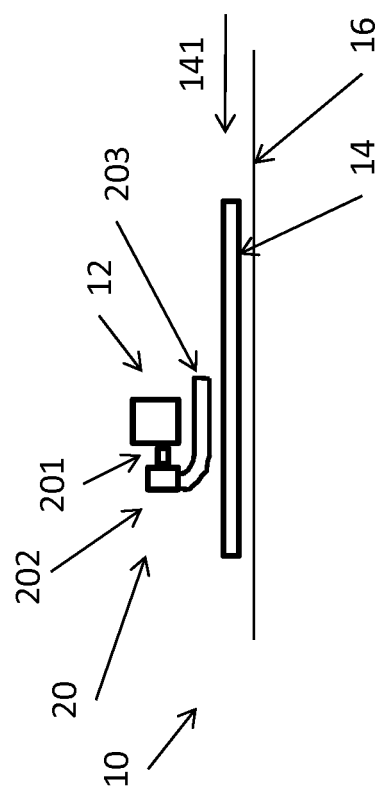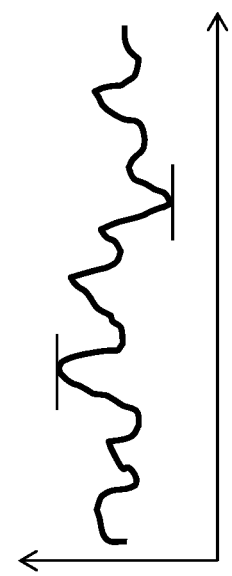

SYSTEM AND A METHOD FOR IRRADIATING AN OBJECT

CROSS REFERENCE TO RELATED APPLICATIONS

This is a national stage filing in accordance with 35 U.S.C. § 371 of PCT/EP2018/060305, filed Apr. 23, 2018, which claims the benefit of the priority of European Patent Application No. 17168782.5, filed Apr. 28, 2017, the contents of each are incorporated herein by reference.

The present application relates to a system and a method of irradiating an object, such as to treat a surface or cure a coating of the object, to sterilize the object or perform other radiation induced modifications of the object.

Radiating systems may be seen in US2013/0026381, U.S. Pat. Nos. 4,665,627, 656,656, 6,555,823, 9,448,108, JP2005/319172, US2017/105257, U.S. Pat. No. 4,028,587, US2003/039579, US2005/031485 and US2004/0035529.

In a first aspect, the invention relates to an irradiating system comprising:
- an elongate radiating element having a longitudinal axis and being configured to output radiation from a multiple positions thereof and in a first direction away from the longitudinal axis,
- a transporting element configured to transport one or more objects in a second direction and past the radiating element to have the object(s) irradiated by the radiation,
- a sensor configured to sense a parameter of the radiation, the sensor comprising a collecting element,
- a translator configured to translate the collecting element along the longitudinal axis and at a position between the radiating element and the transporting element.

In the present context, an irradiating system may be any type of system configured to output radiation, such as a radiation delivery system. The radiation may be any type of radiation, such as IR radiation, Near IR radiation, visible light, UV radiation, X-ray radiation, or combinations thereof. The radiation emitted may be of a single wavelength or within one or more wavelength intervals.

The radiation may have different purposes, and the desired or emitted radiation wavelength and/or intensity and dose may be selected to serve that purpose. For some purposes, the wavelength must be correct and for other purposes, the intensity is of more relevance. Thus, for some purposes, control of the intensity and dose may be of interest. For other purposes, control of the wavelength may be of more interest.

The radiating element is configured to output the radiation desired. The radiating element may not be able to vary the wavelength of the radiation output to any degree. Other radiating elements may be capable of varying the wavelength output. Most radiating elements are able to vary or control the intensity of radiation output.

The radiating element is elongate and is configured to output the radiation from a multiple of positions along the longitudinal axis. Radiating elements of this type may be low or medium pressure arc or microwave powered lamps, arc tubes, gas discharge lamps, quartz lamps, Light emitting Diodes—or combinations thereof. The radiating element may be designed elongate in themselves, such as one or more gas discharge lamps. Alternatively, if more limited, small and/or point-source radiation sources are used, a plurality of such radiation sources may be provided along the longitudinal axis. An array of radiation sources may even be used having one or more rows along the longitudinal axis and columns perpendicular to the longitudinal axis and preferably all in a plane of the transporting element or a plane in which the objects are transported while irradiated.

The radiation sources may emit radiation in a number of directions—also away from the objects to be irradiated. Thus, one or more reflectors may be provided to re-direct radiation not emitted in a direction toward the objects.

The first direction often will be a direction from the emitters to the objects. Normally, this direction is a downward direction.

The transporting element may be any type of transporting element. Naturally, what is desired is a relative movement, so the radiating element may alternatively be translated in relation to the objects. The objects may be transported while being irradiated, or the transport may be intermittent where radiation takes place while the objects are stationary.

Often the transporting element is a belt carrier or rollers capable of translating the objects thereon and past the radiating element.

The second direction preferably is a direction at an angle to the longitudinal direction or first direction and often is a direction perpendicular to the first direction and/or the longitudinal direction. Usually, the radiating element is positioned above and perpendicularly to a direction of a transporting belt carrying the objects to be irradiated.

Naturally, the radiating element may be positioned at any angle to the direction of movement of the objects. A smaller angle may expose an object to more radiation.

The sensor may sense or determine any parameter of the radiation, for example. Often, the intensity of the radiation is of interest. In other situations, the wavelength of the radiation may be of interest. In yet other situations, the thermal energy of the radiation may be a desirable parameter, the temperature of the radiation and even the surface temperature of the object.

The temperature may alternative be that of a lamp if desired or a gas (such as air, see also below) at the object surface and/or around the sensor.

A temperature measurement may be obtained by sensing a temperature of a gas.

Alternatively, the temperature may be determined from radiation from an element, such as a lamp or the object, where the sensor may then determine the temperature in a point or over a surface, such as using a thermal camera. The sensor then may be a camera type, such as based on a CCD, which views the object/lamp, such as via a bundle of optical wires. The optical wires may be ordered so as to be image forming, so that the camera views the lamp/object in the same manner as via a lens. A non-image forming optical wire bundle may have one relation between the ends of the wires at one end and another relation at the other end.

Alternatively or additionally, the sensor may sense a parameter relating to a gas. It may be desired that the irradiation takes place in a specific atmosphere, such as a Nitrogen atmosphere or at least an oxygen free or oxygen depleted atmosphere. Thus, it may be desired to determine e.g. an oxygen partial pressure or a partial pressure of another gas, such as Nitrogen, in order to derive information relating the overall effect or function of the irradiation. Gas sensors are widely known, such as in production plants, engines or the like. A temperature of the gas may also be of interest.

Multiple sensors may be provided if multiple parameters are desired.

The translator may be any type of element which can translate the collecting element. Often, translators are embodied as elements running over or being controlled by a longitudinal rail, but other embodiments may be used if desired.

The translator translates the collecting element along the longitudinal direction of the radiating element so that the collector is translated in a space between the radiating element and the transporting element. The collector may be positioned between the radiating element and the objects to be irradiated. In that manner, a true value of the desired parameter may be obtained—and even along the direction of the radiating element.

The collector may collect or block a portion of the radiation emitted by the emitting element and toward the objects. This may be accounted for by controlling the emitting element and/or the transporting element.

Situations may exist where dirt or debris is dislodged from the objects to be radiated. Such dirt or debris may settle not only on the radiating element, locally affecting the radiation output, but also on the collecting element. Thus, in one embodiment, the translator is configured to translate the collecting element to a position outside of a space between the radiating element and the transporting element.

This position may be along the longitudinal direction but to a position not over the transporting element and/or under the radiation element.

This position may be a resting position where the collector is stored or located when not in use being translated in the space between the radiating element and the transporting element or the transported objects.

At this position, a housing or cleaning station may be provided for the collecting element so as to protect it from dust/debris or the like to keep it operational.

In addition or alternatively, a cleansing element may be provided for cleansing an outer surface of the collecting element, such as in the resting position.

A cleansing element may be a brush or the like, if the most common contamination of the collecting element is a solid material easily removed. Alternatively, the cleansing element may provide a liquid, such as a solvent, to the collecting element, if such cleansing is desired.

The cleansing element may be operable at any point in time or at any position of the collecting element, such as the position described above.

In one embodiment, the sensor is configured to determine a representation of the parameter, such as a partial pressure of a gas or an intensity of radiation emitted and as a function of position along the longitudinal direction. This representation may be presented as a graph or a plurality of values describing the pressure/intensity at individual positions along the longitudinal direction. Naturally, any other parameter of the radiation, such as a wavelength, wavelength interval, temperature or the like, may be represented in the same manner.

This representation reveals a number of interesting facts about the radiating element, the resulting radiation or the result of the irradiation. A simple, derivable fact is whether the radiating element is contaminated or defect. Then, also from the representation, such contamination or defects may be localized. Then, the radiating element may be cleansed. Contamination may affect the radiation output.

If the desired radiation has a certain minimum or maximum intensity, the representation will reveal whether the desired irradiation takes place. Often, the desired parameter is not intensity but actually radiation dose, such as when curing an ink/coating or treating a surface. Thus, if the intensity is too low, the transport velocity may be reduced to increase the overall dose delivered to a desired value.

However, if the intensity is low at only a portion of the longitudinal radiating element and high at other positions, reducing the velocity may bring about a too high dose at other positions along the radiating element. Thus, from the representation, a desired velocity of the transporting may be determined.

However, also a quality of the irradiation may be determined, where quality may be quantified from e.g. the dose delivered or the intensity output. Often, the same intensity/dose is desired along the full length of the radiating element. Thus, the highest quality may be output if the intensity/dose is linear and/or constant in the representation. The less linear the representation, the lower the quality. Also, an unacceptable quality may be seen, if the intensity/dose exceeds a higher threshold value or falls below a lower threshold value.

In the curing situation, a too low intensity or dose will not cure the surface/coating sufficiently, which may render the hardened objects useless. The same may be the situation for other effects obtained by the radiation in/on the objects. A too high intensity/dose may on the other hand discolour or directly destroy the objects again rendering them useless.

If the radiating element has a too high variation along its length and/or if the quality is found too low, the radiating element may be replaced or cleansed.

Thus, the sensor may be configured to determine, as the parameter, one or more of the group consisting of: a lowest sensed radiation intensity, a highest sensed intensity, a difference between a highest and a lowest sensed intensity.

Sometimes, however, the radiating element comprises:
  a plurality of radiation emitters positioned sequentially along the longitudinal direction and
  a power supply individually supplying power to each radiation emitter.

In such situations, individual radiation emitters may be replaced if desired. Alternatively, if a radiation emitter outputs insufficient intensity, for example, it may be separately controlled to output more intensity.

Another solution is one where the sensor is configured to:
  as the parameter, sense the intensity output from the emitters
  identify a first emitter outputting insufficient intensity and output first information relating to one or more emitters adjacent to the first emitter as well as second information relating to an intensity increase desired from the adjacent emitter(s).

Thus, if the faulting or polluted radiation emitter is not able to output the desired intensity, the neighbouring emitter(s) may be controlled to output more radiation to compensate for the faulting emitter. This solution may be chosen where output characteristics of the emitters overlap so that the resulting intensity at the transported objects is more even.

In fact, the output of the sensor may be used for ensuring that the output of the radiation element is the same, within a predetermined margin, along the longitudinal axis. This may be obtained by either identifying the portion of the radiation element which has the lowest output and control all other parts, such as other radiation emitters, to output the same amount of radiation.

Alternatively, the output may be controlled to be a predetermined value, where the controlling may then be a reduction of output of some portions of the radiating element and an increase in the output of others if required.

Having then controlled the output of the radiating element, the overall radiation dose impinging on the objects may be controlled by the transporting velocity of the objects.

Another interesting parameter may be a parameter of gas, such as a temperature thereof or a partial pressure of a gas, such as Oxygen, Nitrogen or a solvent, which will provide information relating to the process caused by the irradiation of the objects. The partial pressure of Oxygen may be desired below a predetermined limit, the partial pressure of Nitrogen may be desired above a certain limit, or the pressure of a solvent (removed from the objects, for example) may be desired above a certain limit in order to know that the function of the irradiation is sufficient.

Often, the irradiation of the objects is very swift, so that it is important that it takes place under the correct circumstances in order to be sufficient. This may be checked and ensured by checking and controlling the partial pressures. If a partial pressure has been found outside a desired interval or below/above a particular limit, a gas providing system may be controlled to e.g. provide more or less gas to the space between the radiating element and the transporting element or the objects, or even to provide more or less gas to a particular portion of this space. The gas providing system may be configured to provide gas to this space at a number of positions, so that the gas providing can be controlled at individual positions.

Also, if a gas parameter is outside of the desired value(s), the transporting element may be controlled (speed down/ stop) as may the radiating element (more intensity/less intensity/stop irradiating). Thus, the gas sensing may stop irradiation until the gas parameter again is within the desired value(s).

In one embodiment, the radiating element comprises an array of radiation emitters positioned in columns and rows, the rows being parallel to the longitudinal axis and the columns perpendicular thereto and preferably parallel to the second direction. Thus, each position of an object is irradiated by all emitters of a column.

Thus, if an emitter of a column is faulting or polluted, the other emitters of that column may be controlled to compensate for the lower emission from the faulting emitter. Naturally, emitters in the rows may also be controlled to compensate for the low performing emitter.

In that situation, the collector may be capable of not only collecting radiation from all of the radiating element at a given position along the longitudinal axis but also from different positions along the second direction so as to be able to determine whether an emitter of a column fails. Alternatively, all emitters in a column may be controlled to output more radiation. The faulting emitter may not do so, but others will.

Actually, a radiation emitter may be controlled in different manners. A usual manner is to adapt a power supply (voltage, current and/or frequency) feeding the radiation emitter or radiating element. Another manner is to control a temperature of the radiation emitter. The temperature may be controlled by controlling a cooling of the radiation emitter. It is known that by varying the temperature of a radiation emitter, the wavelength of the radiation output may be controlled.

In a preferred embodiment, the collecting element is an elongate element configured to guide radiation received thereby toward a sensing element configured to sense the radiation and output a corresponding signal. Naturally, the sensor may be translated together with the collector, and the collector may simply be e.g. a window so that the sensor is in fact translated within the space between the radiating element and the transporting element. An advantage, however, of the collecting element is that the sensor may be positioned in a position not receiving the radiation from the radiating element, such as outside of the space between the radiating element and the transporting element.

The collecting element may e.g. comprise a reflector configured to receive radiation from the radiating element and re-direct this radiation toward the sensing element. Then, the reflector may be configured to receive radiation from a predetermined portion of the radiating element, such as one or more columns as described above or a portion of a column only.

The collecting element may have the function of an optical fibre or waveguide. The collecting element may be self-supporting or may comprise a supporting structure, such as a tube, rod or element or a metal, such as aluminium, steel or a rod having a coating of a metal, such as gold, silver, aluminium or the like. A coating may be a thermal shield or a radiation shield preventing radiation from entering the rod/tube at positions where this is not desired. Openings may then be made in the rod or coating at the position(s) where it is desired to have radiation, gas or the like enter the rod or elongate element.

The elongate element may be configured to sense or receive the parameter at one position along its length—or at multiple positions. Thus, the elongate element may be configured to sense or receive radiation at a multiple of positions along its length. In one situation, the positions may be defined by openings in a metal tube or in a coated tube, where e.g. radiation may enter into the tube. The radiation/ gas may be guided by the tube itself, such as by a coating of the tube (internally and/or on the outside). If radiation is desired in the tube, optical elements, such as prisms or mirrors, may be provided for guiding radiation from the opening(s) along the tube. Alternatively optical fibres may be provided for guiding radiation from an opening and inside the tube.

In one situation, an image forming bundle of fiber optical cables are used for providing to a sensor an image of the lamp/object, where individual fibres may transport what would be a pixel in the image.

As mentioned above, multiple elongate elements may be provided, such as with different characteristics, if desired. Alternatively, an elongate element may be provided having multiple arms (such as a trifork) where the openings are in the arms and the stem is provided at the sensor.

Alternatively, the collecting element may simply be a rod transparent to radiation output of the radiating element. For UV radiation, a suitable rod material may be quartz, fused quartz, synthetic quartz, borosilicate, ceramics as well as a wide range of glass types. Additionally, materials may be selected from the types of materials used for optical elements, such as fibres, lenses, windows or the like for the wavelength range in question.

The rod may be provided by different materials defining a variation in refractive index assisting in guiding the radiation in the rod.

The rod may have any desired cross section, such as circular, oval, triangular, rectangular, or the like.

The collecting element may comprise a coating at predetermined portions thereof to ensure that no radiation enters the rod from undesired directions (such as from below and/or the sides when the rod is translated below the radiating element). Additionally or alternatively, the sensing element may comprise an optical or other filter for removing undesired radiation or the effect thereof before determining the parameter of the radiation.

Naturally, not only an intensity or the like may be determined. If desired, the wavelength may be determined, or an intensity of radiation having a particular wavelength or within a particular wavelength interval may be determined. In fact, a wavelength spectrum may be determined if desired, if for example the sensing element may be a spectrometer.

When the desired parameter relates to a gas, the collecting element may be a tube or the like, where the sensor may comprise a pump or other element configured to provide a gas flow in the tube. A flow may also be generated by a pressure in the space between the radiating element and the transporting element being higher than at the surroundings. The sensor then may comprise a gas sensor for determining the parameter of interest, such as a partial pressure of a particular gas or molecule or the presence of a gas or molecule.

In one embodiment, it is desired to derive a parameter of the objects irradiated. To that effect, radiation may be received from such objects to derive that parameter. This collection may be performed using the above collector if desired. In that situation, and if the collector is configured to also receive radiation from the radiating element, the sensing element may be configured to separate the radiation from the objects and the radiating element—or distinguish between the contributions from the two radiation sources.

Alternatively, the system may comprise an additional collector configured to be translated along the longitudinal direction and which is configured to receive radiation from the objects and feed this radiation to the same or an additional sensor configured to output a parameter relating to the objects. The additional collector may be as that described above, potentially adapted to the radiation desired sensed.

Often, the radiation from the radiating element will impinge on the collector(s) from one direction and that from the objects from another, usually directly opposite, direction. Thus, the structure of an additional collector may be rotated or otherwise adapted to this other radiation direction.

The radiation from the objects may be used for determining, quantifying or estimating a number of parameters such as the gloss of a surface/coating/ink thereof, a degree of curing thereof, a temperature or the like thereof. In addition, a colour of the object may be determined, to be able to determine any colour variation over the object or over time. In another situation, holes in the objects or the coating may be detected and/or knots may be detected either from colour variations or e.g. variations in the surface, such as a reduced surface smoothness. Colour detectors and defect detectors (surface smoothness detectors) are known.

Further below, different manners of determining such parameters are described using e.g. radiation from the elongate radiating element or a separate radiation/light emitter.

In one embodiment, a 3D dose profile is determined for a lamp. Thus, the radiation intensity at different angles from the lamp, such as in different planes perpendicular to the object and at different distances to the lamp, may be provided, preferably for different intensities, as the profile may change with the intensity. Then, from an intensity determined by the sensor, the total dose may be determined which is received by a portion of the object when travelling past the lamp. In this situation, the velocity with which the object passes the lamp may be taken into account—or controlled.

In another situation, the ventilation or gas concentration and concentration profile in a space between the object and the lamp may be determined or monitored. This may be of great importance when this atmosphere is crucial to the process, typically curing but perhaps also sterilization, taking place.

Clearly, the information obtained by the present system may be used for e.g. controlling the velocity at which the objects pass the lamp. However, other process parameters may also or alternatively be controlled. The velocity determined may be used for controlling other systems, such as the system coating the objects or even the system preparing the objects for coating.

In one example, the gloss or surface smoothness of the coated objects may depend on the quality of preparation of the objects for the coating. Thus, if a sanding machine is not optimal, the final surface of the hardened objects may be too rough. This may be detected by the present system and be used for either altering the operation of the preparing system, such as a sanding machine, or for informing an operator that the preparing system requires attention.

In one embodiment, the invention relates to a sensor travelling along the UV or UV LED light source while sampling the intensity of the light from the source. This can be done between the UV or UV LED Light source and the product the UV or UV LED source is intended to irradiate. The collected data can then be used to either display the status or adjust the light source to a desired level or profile which is then displayed.

A second aspect of the invention relates to method of operating the system according to the first aspect, the method comprising:
 the transporting element transporting objects in the second direction,
 the radiating element emitting the radiation in the first direction,
 the translator translating the collecting element while the collecting element collects radiation or gas and feeds at least a portion thereof to the sensor,
 the sensor sensing a parameter of the gas/radiation.

Naturally, all considerations, embodiments and situations of the first aspect may be relevant also in relation to the second aspect.

Thus, the transporting step may comprise transporting the elements at a predetermined velocity, which velocity may be varied as a response to the parameter sensed. The transporting step may comprise transporting the objects while the objects are irradiated. Alternatively, the transport may be performed when the objects are not irradiated so that transport and irradiation are performed sequentially.

In one embodiment, the translating step comprises translating the collecting element to a position outside of a space between the radiating element and the transporting element.

Additionally or alternatively, the method could further comprise the step of cleansing an outer surface of the collecting element. As mentioned above, the cleansing may e.g. be performed by physically removing dust or debris from the surface, such as using a brush or the like. Alternatively, a chemical cleansing may be used, where e.g. a solvent or detergent is provided on the surface.

In one embodiment, the sensing step comprises determining a representation of an intensity of radiation emitted as a function of position along the longitudinal direction. The parameter may be derived from this representation, such as a maximum or minimum, or a difference between the max and min values.

The parameter may describe a linearity of this representation, as in many situations, the same intensity or the like is desired along the length of the radiating element, or at least a large portion thereof.

As described above, the radiating element may comprise:
 a plurality of radiation emitters positioned sequentially along the longitudinal direction and a power supply individually supplying power to each radiation emitter.

In that situation, the sensing step may comprise:

sensing, as the parameter, an intensity output from the emitters, identifying a first emitter outputting insufficient intensity and outputting first information relating to one or more emitters adjacent to the first emitter as well as second information relating to an intensity increase desired from the adjacent emitter(s).

The control may also or additionally be performed by controlling a temperature of the radiation emitters.

In general, as is also described above, many manners exist of controlling such emitters to compensate for an underperforming emitter.

As described above, the collector and sensor may additionally or alternatively relate to parameters of a gas present between the radiating element and the transporting element. Thus, the parameter determined along the longitudinal direction may be that of a gas, and the controlling, if performed, may relate to the output of the radiating element, the transport of the transport element or a gas flow of a desired gas to the space between the radiating element and the transporting element.

The method may also comprise receiving radiation from the objects and deriving any of the information and parameters described above and below.

In the following, preferred embodiments of the invention will be described with reference to the drawing, wherein:

FIG. 1 illustrates a system according to the invention seen from the front,

FIG. 2 illustrates the system of FIG. 1 seen from the side,

FIG. 3 illustrates an output type of the sensor element and

FIG. 4 illustrates a sensor comprising multiple elongate radiation receivers/guides.

In FIG. 1, a standard radiating system 10 is seen having an elongate radiation emitting element 12, such as a UV lamp comprising one or more elongate emitters which may be UV LEDs or more old-fashioned emitters. The emitters may be formed as individual blocks 121 of emitters which are assembled to a desired length.

Objects 14 to be irradiated are transported below the element 12 on a carrier band 16. The irradiation may be to cause a coating or ink to cure, to sterilize the objects or e.g. to modify a surface of the objects 14 or the like. The radiation impinging on the objects may be used for generating any desired effect in or on the objects. A coating on or of the objects may be affected, such as cured, or the surface may be sterilized or otherwise modified. Surface characteristics of the objects, such as gloss, surface tension or the like may also be affected by the radiation. Polymers may be cross-bound by the radiation if desired. Thus, all known radiation induced reactions may be controlled using the present set-up.

The objects 14 are transported at a velocity ensuring, under normal circumstances, sufficient curing/sterilization/treatment of the objects 14, but this often requires that the intensity of the radiation 18 is within a desired interval or above a lower limit.

Radiation emitters may fade over time or become inoperable. Some emitters have a built-in sensor providing an output of the intensity output of this particular emitter.

However, the emitters may also be covered by dirt or debris, reducing the overall intensity output in the direction toward the objects. A built-in sensor would not sense this.

In the present embodiment, a sensor 20 is provided which is translatable along a guide 201 along the longitudinal length of the emitter 12 while having (see also FIG. 2) an elongate radiation receiver or guide 203 extending below the emitter 12, the receiver/guide 203 collecting radiation from below the emitter 12 and feeding it to a sensor element 202.

In this manner, the actual radiation intensity output may be determined along the length of the emitter. From an output of the sensor element, information may be derived as to the state of the emitter 12 and/or the quality of the curing/treatment/sterilization taking place.

The guide 203 may simply be a transparent rod collecting whatever radiation is impingent. The rod may have across its cross section a variation in refractive index in order to better guide radiation. Alternatively, the outer edges of the rod may be surrounded by e.g. air generating the desired index difference.

In other embodiments, the guide may comprise e.g. a mirror or other reflector for directing radiation from a predetermined direction, such as an upward direction, toward the sensor element. Then, no refractive index change may be required to guide the radiation to the sensor element.

The output may be a simple graph as seen in FIG. 3 illustrating an output of the sensor 202 as the receiver/collector 203 is translated along the length of the receiver. This output may be representative of an intensity of the radiation at the individual positions along the longitudinal direction.

From the output, a number of types of information may be derived. Firstly, the intensity itself may be estimated at different positions. This intensity may directly relate to the quality of the curing of the coatings/inks on the elements, the surface modification or the sterilization of objects. As the intensity may vary along the length of the emitter, so may the quality of the curing/modification/sterilization. A desired intensity interval may be set for optimal curing. If the intensity at a position along the longitudinal axis falls outside of the interval, an un-optimal curing (or other treatment) may be obtained. Thus, non-cured objects may be obtained, or objects may be obtained which have received too much radiation. Too much radiation may heat the object too much and thus damage it.

The output may itself be used for a quantitative determination and thus for e.g. controlling the speed of the belt, such as from a maximum or minimum value of the output. Alternatively, the mere variation of the output of the sensor may be used to give a general idea of the state of the system but other sensors may be used to sense the actual intensities output.

Clearly, the intensity or dose of radiation received may also depend on the velocity of transport of the objects 14 by the belt 16. Thus, if a too high intensity is generally experienced by the sensor, the velocity of the belt 16 may be increased. However, if parts of the emitter output too low intensity, that would then bring parts of the elements or parts of the emitter outside of the desired range.

From the output of the sensor, different quantifications or parameters may be obtained depending on the situation. In some situations, it is merely desired that the lowest intensity is known. Then, the output may be analyzed to determine the lowest value (indicated in FIG. 3). In other situations, the highest intensity is of interest and in yet other situations, the difference between the highest and lowest intensities may be of interest.

Such parameters may be used for determining a state of the system, such as if the emitter 12 or a portion 121 thereof is to be replaced or if cleaning, compensation or alteration is required to bring the intensity within the desired regime again.

In one situation, the emitter 12 comprises a number of smaller emitters, such as LEDs along the longitudinal direction. Thus, if one LED is defect or has a lower emission, neighbouring LEDs may be controlled to output more radiation to compensate for the lower emission from the less performing LED. This situation may be identified in the output of FIG. 3 as a dip in intensity. The faulting LED or position may be determined as may the neighbours which may then be operated to output a higher intensity. Once the compensating scheme is determined, the sensor may be operated again to ensure that the compensation takes place as desired.

Alternatively or additionally, the lowest value, highest value, mean value or difference value may be used for alarming an operator to take action.

Naturally, not just a single emitter may be provided at each position along the longitudinal direction. The emitter may comprise an array of emitters having rows along the longitudinal direction and columns perpendicular thereto (the array being parallel to the plane wherein the elements 14 are transported.

Thus, if a column is identified from which the intensity is too low (or too high), the neighbouring columns may be operated to compensate.

As described above, any intensity pattern or curve may be obtained along the longitudinal axis. A constant intensity is usually desired. Thus, the elongate radiating element or the emitters may be controlled to arrive at the desired intensity by e.g. increasing or lowering the intensity output at particular positions. This intensity may be that of a portion or emitter outputting the least intensity or a predetermined intensity where, if a portion or emitter is not able to output that intensity, neighbouring emitters or portions may have their intensity increased to arrive at the desired intensity.

Instead of actually taking action on the basis of the representation of the information, the representation may simply be stored in order to document the operation of the system.

In fact, the collector/guide may be able to determine the intensity also at different positions along its length, whereby the particular faulting LED in the column may be determined. Then, the other LEDs of the column may additionally or alternatively be used for compensating.

The receiver/guide may be a single rod of a material transmissive to the wavelength(s) output by the emitter. Alternatively, the receiver/guide may comprise a number of individual guides, such as individual guides collecting radiation at different positions along the length of the element 203, so that not only can the complete intensity output from a position along the longitudinal direction of the emitter be determined but also the intensity profile perpendicular thereto (along the length as seen in FIG. 2).

Naturally, after correction, the collector may be translated again and the information re-determined to ascertain that the correction was performed as desired.

It may be possible that the guide 203 itself may also be contaminated. Thus, it may be desired that the guide, when not translated between the emitter and the band, is moved into a protective housing 204 which may be positioned outside of (along the longitudinal direction) the area between the belt and emitter so as to not block the radiation when not operating.

Additionally or alternatively, the guide may be cleansed at regular intervals or after/before each use, such as by cleansing brushes, cleansing fluid or the like.

In order to take into account any damage, dirt, aging or the like on or of the guide, the sensor may output information relating to a relative measurement.

Thus, the guide may be translated from one end of the emitter to the other and back again and calibration measurements may be made before translating the guide and after. If a too large difference exists, the guide may need replacing.

Also, any difference may be used for correcting the output of the sensor, such as the graph of FIG. 3.

Alternatively, a calibration emitter may be provided (not illustrated) in the housing 204 so as to provide a measure of the state of the guide. The read-out of the sensor may thus be used for correcting the output of the sensor when the guide is translated. In that manner, the output of the sensor may be quantified to read-out fx the actual intensity output.

Naturally, the sensor may be used for sensing other parameters than the intensity output, such as a wavelength output, wavelength interval or the like output, or a spectrum of the radiation output. Emitters may vary not only or not at all in intensity but in wavelength. A shift in wavelength may also give a variation in the curing/modification/sterilization performed.

On one embodiment, the guide 203 may be used for sensing not parameters of the radiation 18 of the emitter but a parameter of the objects 14. The guide thus may be configured to receive radiation from the objects 14. Naturally, both radiation from the emitter 12 and the objects 14 may be desired sensed. This may be obtained using the same collector.

Alternatively, as is illustrated in FIG. 4, another radiation collector or guide 205 may be provided which may be configured to receive radiation from the objects 14. The guides 203 and 205 may be configured to receive radiation from different directions (one from a downward direction and the other from above) or may be configured to guide radiation of different wavelengths. Alternatively, the sensor element 202 may be configured to filter, from the received radiation, the radiation desired for the intensity output and the parameter of the objects 14. The guide 205 may be of the general types described above.

One parameter of interest of the objects 14 is gloss. The gloss of the objects may be affected by the intensity of the radiation impinging on the objects. Variation in the irradiation may result in a variation in gloss. Gloss is often measured as relative reflection of radiation/light (UV or visible) at a defined angle.

Radiation reflected from a particular angle may be determined by a collector or detector aimed in a predetermined angle toward the objects or the transporting element. Such aiming may be obtained using e.g. a lens, an aperture or the like.

The radiation thus detected may be generated by the elongate radiating element, if the direction is selected so that radiation emitted by the radiating element may be reflected under the desired angle and toward the collector/detector.

Alternatively, a separate light/radiation source may be positioned so as to emit radiation or light on to the objects under the desired angle and so that the reflected radiation/light impinges on the collector/detector. In this situation, the separate light/radiation source may be translated along with the collector/detector, such as if also attached to the translator.

When a separate light/radiation source is used, a wavelength may be used which is not output from the elongate radiating element. This facilitates separation, if required, of the radiation from the elongate radiation source and the separate light/radiation source.

A wide range of parameters may be determined from the objects based on radiation emitted/reflected/scattered therefrom or thereby. One parameter of interest of the objects 14 is the degree of hardening/curing. One advantage of radiation hardening/curing is that the hardened objects may be immediately stacked or touched, but this requires that the hardening is sufficient. Hardening may be determined or quantified from the number of residual double bonds in the object/coating/paint/surface. The fewer residual doublebonds, the higher the degree of curing.

Double bonds may be quantified in a number of manners, one being based on the infrared absorption spectrum of the surface/coating/ink. From this spectrum, such as using Fourier transformation, an estimate of the degree of curing may be obtained.

For this determination, radiation from the elongate radiating element may be used, or again a separate radiation emitter may be provided for launching radiation on to the objects. The absorption may be determined or estimated from radiation reflected by the objects.

Also, fluorescence may be used for determining the degree of curing. See e.g. "Characterization of Photocurable Coatings Using Fluorescence Probes", Song et al, Naval contract N00014-93-1-0772.

Naturally, also other parameters of the objects may be determined from radiation output thereof, such as a surface temperature of the object or of the lamp.

Another feature would be colour or colour differences and/or surface imperfections of the objects. Surface imperfections and colour differences may stem from imperfect coating thereof and/or knots in underlying wood. Colour differences may be caused by imperfect coating or imperfect treatment, such as curing.

In another embodiment, the irradiation is desired performed in a particular atmosphere, typically an oxygen free or oxygen depleted atmosphere. Thus, a particular gas, often Nitrogen, is fed to the space between the radiating element and the objects. This gas may be fed into this space at a number of locations along the longitudinal direction.

In this situation, the collector and sensor may be configured to determine a gas parameter, such as a partial pressure or temperature, to arrive at a representation of this parameter long the longitudinal directions.

The gas may be oxygen, the gas input (nitrogen) or a gas emitted by the objects during irradiation, for example.

This representation may be compared to minimum and/or maximum values. This representation may be used for varying the gas introduction at positions at which the gas pressure determined is not desirable. Alternatively, the representation may be used for varying the irradiation or transport if desired.

The gas may be fed to a space between the radiating element and the objects/transporting element especially if a shroud or the like is provided sealing this space from the surroundings (while allowing the objects to enter/exit this space). The gas may be fed to this space via one or more openings into this space, where flow controllers preferably are provided for individually controlling the flow into each of these openings so that a variation (along the length) of a gas pressure for example may be compensated for by varying the gas pressure at an identified opening.

The invention claimed is:

1. An irradiating system comprising:
   an elongate radiating element having a longitudinal axis and being configured to output radiation from multiple positions thereof and in a first direction away from the longitudinal axis,
   a transporting element configured to transport one or more objects in a second direction past the radiating element to have the object(s) irradiated by the radiation,
   a sensor configured to sense a parameter, the sensor comprising a collecting element,
   a translator configured to translate the collecting element along the longitudinal axis and at a position between the radiating element and the transporting element.

2. An irradiating system according to claim 1, wherein the translator is configured to translate the collecting element to a position outside of a space between the radiating element and the transporting element.

3. An irradiating system according to claim 1, further comprising a cleansing element configured to cleanse an outer surface of the collecting element.

4. An irradiating system according to claim 1, wherein the sensor is configured to determine a representation of an intensity of radiation emitted as a function of position along the longitudinal direction.

5. An irradiating system according to claim 1, wherein:
   the radiating element comprises:
   a plurality of radiation emitters positioned sequentially along the longitudinal direction and
   a power supply individually supplying power to each radiation emitter,
   the sensor is configured to:
   as the parameter, sense the intensity output from the emitters
   identify a first emitter outputting insufficient intensity and output first information relating to one or more emitters adjacent to the first emitter as well as second information relating to an intensity increase desired from the adjacent emitter(s).

6. An irradiating system according to claim 1, wherein the sensor is configured to determine, as the parameter, one or more of the group consisting of: a lowest sensed radiation intensity, a highest sensed intensity, a difference between a highest and a lowest sensed intensity.

7. An irradiating system according to claim 1, wherein the collecting element is an elongate element configured to guide radiation received thereby toward a sensing element configured to sense the radiation and output a corresponding signal.

8. An irradiating system according to claim 1, wherein the collecting element is a rod transparent to radiation output of the radiating element.

9. An irradiating system according to claim 1, further comprising an additional sensor configured to be translated along the longitudinal direction and which is configured to receive radiation from the objects and output a parameter relating to the objects.

10. A method of operating the system according to claim 1, the method comprising:
    the transporting element transporting elements in the second direction,
    the radiating element emitting the radiation in the first direction,
    the translator translating the collecting element while the collecting element collects radiation or gas and feeds at least a portion thereof to a sensing element of the sensor, the sensor sensing a parameter of the radiation or gas.

11. A method according to claim 10, wherein the translating step comprises translating the collecting element to a position outside of a space between the radiating element and the transporting element.

12. A method according to claim 11, further comprising the step of cleansing an outer surface of the collecting element.

13. A method according to claim 10, wherein the sensing step comprises determining a representation of an intensity of radiation emitted as a function of position along the longitudinal direction.

14. A method according to claim 10, wherein:
the radiating element comprises:
a plurality of radiation emitters positioned sequentially along the longitudinal direction and
a power supply individually supplying power to each radiation emitter,
the sensing step comprises:
sensing, as the parameter, an intensity output from the emitters
identifying a first emitter outputting insufficient intensity and
outputting first information relating to one or more emitters adjacent to the first emitter as well as second information relating to an intensity increase desired from the adjacent emitter(s).

15. A method according to claim 10, wherein the sensing step comprises determining, as the parameter, one or more of the group consisting of: a lowest sensed radiation intensity, a highest sensed intensity, a difference between a highest and a lowest sensed intensity.

\* \* \* \* \*